(12) United States Patent
Ise et al.

(10) Patent No.: US 9,175,084 B2
(45) Date of Patent: Nov. 3, 2015

(54) DIAGNOSTIC MARKER FOR EFFECT OF ANTICANCER AGENT

(75) Inventors: Nobuyuki Ise, Tokyo (JP); Daisuke Nambara, Tokyo (JP); Kazuya Omi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 13/635,911

(22) PCT Filed: Mar. 18, 2011

(86) PCT No.: PCT/JP2011/056545
§ 371 (c)(1),
(2), (4) Date: Sep. 19, 2012

(87) PCT Pub. No.: WO2011/125458
PCT Pub. Date: Oct. 13, 2011

(65) Prior Publication Data
US 2013/0029357 A1    Jan. 31, 2013

(30) Foreign Application Priority Data

Apr. 2, 2010   (JP) ................... 2010-085723

(51) Int. Cl.
| | |
|---|---|
| A61K 35/12 | (2015.01) |
| C07K 16/28 | (2006.01) |
| G01N 33/50 | (2006.01) |
| G01N 33/574 | (2006.01) |
| C12Q 1/48 | (2006.01) |
| G01N 33/566 | (2006.01) |

(52) U.S. Cl.
CPC ............ *C07K 16/2863* (2013.01); *C12Q 1/485* (2013.01); *G01N 33/5011* (2013.01); *G01N 33/566* (2013.01); *G01N 33/574* (2013.01); *G01N 33/57423* (2013.01); *G01N 33/57492* (2013.01); *G01N 2500/00* (2013.01); *G01N 2800/44* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,871,959 A | 2/1999 | Rong et al. | |
| 2005/0054019 A1 | 3/2005 | Michaud et al. | |
| 2007/0037209 A1 | 2/2007 | Gherardi | |
| 2009/0226443 A1* | 9/2009 | Filvaroff et al. | |
| 2010/0040629 A1 | 2/2010 | Michaud et al. | |

FOREIGN PATENT DOCUMENTS

| | | |
|---|---|---|
| JP | 2007 501013 | 1/2007 |
| JP | 2009-526010 | 7/2009 |
| WO | 2007 056523 | 5/2007 |

OTHER PUBLICATIONS

Cappuzzo et al, Annal of Oncology 20:298-304, 2009, published online Oct. 2008.*
Athauda et al, Clin Cancer Res 12(14): 4154-4162, 2006.*
Christensen et al, Cancer Letter 225:1-26, 2005.*
Cipriani et al, Lung Cancer 63:169-179, Feb. 2009.*
Extended European Search Report issued on Nov. 21, 2013 in Application No. 11765360.0.
Cipriani Nicole A., et al., "MET as a target for treatment of chest tumors", Lung Cancer, Elsevier, vol. 63, No. 2, XP025859951, Feb. 1, 2009, pp. 169-179.
Ryan E. Lawrence, et al., "MET molecular mechanisms and therapies in lung cancer", Cell Adhesion & Migration, vol. 4, No. 1, XP055087639, Jan. 1, 2010, pp. 146-152.
Pasi A. Janne, et al., "Factors underlying sensitivity of cancers to small-molecule kinase inhibitors", Nature Reviews Drug Discovery, vol. 8, No. 9, XP055087702, Sep. 1, 2009, pp. 709-723.
Office Action issued Dec. 16, 2014 in Japanese Patent Application No. 2012-509386 (with English translation).
Engelman, J.A., et al., "MET Amplification Leads to Gefitinib Resistance in Lung Cancer by Activating ERBB3 Signaling," Science, vol. 316, No. 5827, pp. 1039-1043 (May 18, 2007).
Athauda, G., et al., "c-MET Ectodomain Shedding Rate Correlates with Malignant Potential," Clinical Cancer Research, vol. 12, No. 4, pp. 4154-4162, (Jul. 15, 2006).
Yano, S., "Haigan no Bunshi Seibutsugaku to Bunshi Hyoteki Chiryo no Saisentan HGF/MET Signal ni yoru EGFR-TK Sogaiyaku Taisei," Gekkan Kokyuki Naika, vol. 17, No. 3, pp. 283-288, (Mar. 28, 2010).
Shukuya, T., et al., "Hi Sentakuteki Chiryo kara Sentakuteki Chiryo eno Paradigm Shift 2) Koganzai no Sayo Kijo Sonomono o Shuyo Tokuiteki na Mono to suru Hoho 1-c EGFR Sayoyaku irreversible EGFR-TKI ya c-Met Sogaizai nado tono Heiyo," Mebio Oncology, vol. 6, No. 1, pp. 23-31, (2009) (with partial English translation).
Lutterbach, B., et al., "Lung Cancer Cell Lines Harboring MET Gene Amplification Are Dependent on Met for Growth and Survival," Cancer Research, vol. 67, No. 5, pp. 2081-2088, (Mar. 1, 2007).
Mark, M.R., et al., "Expression and Characterization of Hepatocyte Growth Factor Receptor-IgG Fusion Proteins," The Journal of Biological Chemistry, vol. 267, No. 36, pp. 26166-26171, (Dec. 20, 1992).
International Search Report Issued Apr. 26, 2011 in PCT/JP11/56545 Filed Mar. 18, 2011.

* cited by examiner

*Primary Examiner* — Lei Yao
(74) *Attorney, Agent, or Firm* — Oblon, McClelland, Maier & Neustadt, L.L.P.

(57) ABSTRACT

The present invention enables to realize a convenient determination of a therapeutic effect of an anticancer agent on a cancer. Specifically, the present invention provides a diagnostic marker for an effect of an anticancer agent on a cancer, comprising a substance having an affinity for a fragment of an extracellular domain of c-MET; a diagnostic reagent for an effect of an anticancer agent on a cancer, comprising a substance having an affinity for a fragment of an extracellular domain of c-MET and the fragment of the extracellular domain of c-MET; and a method of testing an effect of an anticancer agent on a cancer, comprising (a) measuring a concentration of a fragment of an extracellular domain of c-MET in a biological sample from a subject, and (b) comparing the measured concentration of the fragment of the extracellular domain of c-MET with an indicator which presents a relationship between a concentration of the fragment of the extracellular domain of c-MET and the effect of the anticancer agent on the cancer.

9 Claims, 4 Drawing Sheets

FIG. 4

DIAGNOSTIC MARKER FOR EFFECT OF ANTICANCER AGENT

TECHNICAL FIELD

The present invention relates to a diagnostic reagent and kit for an effect of an anticancer agent, and a method of testing the effect of the anticancer agent.

BACKGROUND ART

Diagnosis of sensitivity and resistance against a specific anticancer agent is important for selecting the specific anticancer agent that is more effective for a specific patient with cancer. Therefore, biomarkers that can diagnose the sensitivity and the resistance against the specific anticancer agent have been actively explored. Examples of such an anticancer agent may include c-MET inhibitors and EGFR inhibitors.

(1) c-MET Inhibitor

It is shown that growth of a certain cancer can be inhibited by inhibiting c-MET (a receptor-type tyrosine kinase) that is one of oncogenes (Non-patent Literature 1), and development of a c-MET inhibitor as an anticancer agent has been advanced. There are many unclear points so far about the cancers that are sensitive against the c-MET inhibitor, which are effectively treated by the c-MET inhibitor, and the cancers caused by hyperactivation of a c-MET gene (e.g., cancers caused by amplification, mutation or the like of the c-MET gene) is promising candidates of the cancers that are sensitive against the c-MET inhibitor.

(2) EGFR Inhibitor

In cancer therapy with a molecular target drug such as an EGFR inhibitor (e.g., gefitinib), an event has become problematic in which a cancer that is effectively treated with the molecular target drug in early times lose its therapeutic effect during a long term treatment because of resistance against the molecular target drug. It is reported that the amplification of the c-MET gene is thought to be one of causes for this event (the amplification of the c-MET gene was confirmed in about 20% of patients with lung cancer which had acquired a resistance to gefitinib) (Non-patent Literature 2). It is also reported that the cancer in which the amplification of the c-MET gene is observed can be treated with simultaneous combination of the EGFR inhibitor and the c-MET inhibitor (Non-patent Literature 2).

Meanwhile, a method of measuring the amplification of the c-MET gene is available as a method capable of selecting the cancer that is sensitive against the c-MET inhibitor and the cancer that is resistant against the EGFR inhibitor. A FISH method capable of directly detecting the gene amplification is known as the method of measuring the amplification of the c-MET gene. However, the FISH method is problematic since it requires cumbersome steps that are treatments of cancer cells and detection of the gene amplification, and is difficult to be automated. Thus, it is expected to develop a method capable of diagnosing the sensitivity against the c-MET inhibitor and the resistance against the EGFR inhibitor conveniently.

Ectodomain shedding that is a phenomenon that a fragment of an extracellular domain of c-MET (a secretory form of c-MET) is released is reported for the c-MET gene (Patent Literature 1). It is also reported that the fragment of the extracellular domain of c-MET can be used as a biomarker for the cancer (Patent Literature 2) and the ectodomain shedding can be associated with malignancy of the cancer (Non-patent Literature 3).

PRIOR ART LITERATURE

Patent Literature

Patent Literature 1: US 2007037209 (A1)
Patent Literature 2: WO2007/056523

Non-Patent Literature

Non-patent Literature 1: Cancer Res., 2007; 67: 2081-2088.
Non-patent Literature 2: Science, 2007; 316: 1039-1043.
Non-patent Literature 3: Clin. Cancer Res., 2006; 12:4154-4162.

DISCLOSURE OF INVENTION

Problem to be Solved by the Invention

It is an object of the present invention to realize a convenient determination for a therapeutic effect of an anticancer agent on a cancer.

Means for Solving Problem

As a result of an extensive study, the present inventors have found that a fragment of an extracellular domain of c-MET can be utilized as a biomarker specific for a cancer that is sensitive or resistant against an anticancer agent. Therefore, the present inventors have conceived that the therapeutic effect of the anticancer agent on the cancer can be determined conveniently by measuring a concentration of the fragment of the extracellular domain of c-MET, and completed the present invention. The aforementioned prior arts do not describe or suggest that the fragment of the extracellular domain of c-MET could be utilized as the biomarker for determining the therapeutic effect of the anticancer agent on the cancer (e.g., sensitivity against the c-MET inhibitor and resistance against the EGFR inhibitor).

Accordingly, the present invention is as follows:

[1] A diagnostic reagent for an effect of an anticancer agent on a cancer, comprising a substance having an affinity for a fragment of an extracellular domain of c-MET.

[2] The diagnostic reagent of the aforementioned [1], wherein the substance having the affinity for the fragment of the extracellular domain of c-MET is an antibody against the fragment of the extracellular domain of c-MET.

[3] The diagnostic reagent of the aforementioned [1] or [2], wherein the anticancer agent is an anticancer agent for a lung cancer.

[4] The diagnostic reagent of any one of the aforementioned [1] to [3], wherein the effect of the anticancer agent is sensitivity against a c-MET inhibitor.

[5] The diagnostic reagent of any one of the aforementioned [1] to [3], wherein the effect of the anticancer agent is resistance against the anticancer agent.

[6] The diagnostic reagent of the aforementioned [5], wherein the anticancer agent is an EGFR inhibitor.

[7] A diagnostic kit for an effect of an anticancer agent on a cancer, comprising a substance having an affinity for a fragment of an extracellular domain of c-MET, and the fragment of the extracellular domain of c-MET.

[8] A method of testing an effect of an anticancer agent on a cancer, comprising the following steps (a) and (b):

(a) measuring a concentration of a fragment of an extracellular domain of c-MET in a biological sample from a subject; and (b) comparing the measured concentration of the fragment of the extracellular domain of c-MET with an indicator which presents a relationship between a concentration of the fragment of the extracellular domain of c-MET and the effect of the anticancer agent on the cancer.

Effect of the Invention

According to the present invention, the therapeutic effect of the anticancer agent (e.g., a molecular target drug such as the c-MET inhibitor or the EGFR inhibitor) on the cancer can be conveniently determined and the therapeutic effect of the anticancer agent on the cancer can be conveniently monitored.

In addition, the present invention is highly reliable upon determining the therapeutic effect of the anticancer agent on the cancer, since a remarkable difference is observed for concentrations of the fragment of the extracellular fragment of c-MET measured between the cancer sensitive against the anticancer agent and the cancer resistant against the anticancer agent, as well as the cancer sensitive against the anticancer agent and the cancer resistant against the anticancer agent can be clearly distinguished by such a remarkable difference according to the present invention.

Furthermore, according to the present invention, the therapeutic effect of the anticancer agent on the cancer can be determined easily, since a large amount of the fragment of the extracellular domain of c-MET is observed in cancer that is sensitive or resistant against the anticancer agent, as well as such a large amount of the fragment of the extracellular domain of c-MET can be measured easily.

EMBODIMENT FOR CARRYING OUT THE INVENTION

The present invention provides a method of testing an effect of an anticancer agent on a cancer. The test method of the present invention may be a diagnosis method or a prediction method.

The test method of the present invention can comprise the following steps (a) and (b):
(a) measuring a concentration of a fragment of an extracellular domain of c-MET in a biological sample from a subject; and
(b) comparing the measured concentration of the fragment of the extracellular domain of c-MET with an indicator which presents a relationship between a concentration of the fragment of the extracellular domain of c-MET and an effect of the anticancer agent on the cancer.

c-MET is a receptor of a hepatocyte growth factor (HGF) and activates an intracellular signaling by binding of HGF. c-MET is composed of the α chain and β chain generated by cleaving a precursor of c-MET (pro c-MET) and forms a dimer by a disulfide linkage. c-MET is a receptor penetrating a cell membrane and the entire α chain and a part of the β chain are present extracellularly (see, e.g., Mark, et al., The Journal of Biological Chemistry, 1992, Vol. 267, No. 36, pp. 26166-26171; Journal of Clinical and Experimental Medicine (IGAKU NO AYUMI), 2008, Vol. 224, No. 1, pp. 51-55). See also GenBank Accession No: NP_000236.2 for human c-MET and its α chain and β chain.

As used herein, the term "fragment of an (the) extracellular domain of c-MET" refers to a polypeptide of the extracellular domain of c-MET which is released by ectodomain shedding, or a degraded product of the polypeptide. In this Specification, the fragment of the extracellular domain of c-MET may be referred to as the secretory form of c-MET.

In the aforementioned (a), the subject may include a mammal that is suffered from the cancer or a mammal that is possibly suffered from the cancer. Examples of the mammal may include primates, pet animals, and working animals. Specifically, examples of the mammal may include humans, chimpanzees, dogs, cats, cattle, sheeps, horses, rabbits, mice, and rats, and the mammal is preferably the human.

As used herein, the term "cancer" refers to a cancer that can be associated with an amplification of a c-MET gene. Examples of such a cancer may include lung cancer (e.g., non-small cell carcinoma such as squamous cell carcinoma, adenocarcinoma and large cell carcinoma, and small cell carcinoma), gastrointestinal cancer (e.g., gastric cancer, small intestine cancer, large intestine cancer, rectal cancer), pancreatic cancer, renal cancer, liver cancer, thymic cancer, spleen cancer, thyroid cancer, adrenal cancer, prostate cancer, urinary bladder cancer, ovarian cancer, uterus cancer (e.g., endometrial cancer, cervical cancer), bone cancer, skin cancer, brain tumor, sarcoma, melanoma, blastoma (e.g., neuroblastoma), adenocarcinoma, squamous cell carcinoma, solid cancer, epithelial cancer, and mesothelioma.

A preferred example of the subject is a patient with cancer for whom the treatment with a specific anticancer agent is considered. Examples of the specific anticancer agent may include a c-MET inhibitor, an EGFR inhibitor, an ALK inhibitor, a PDGFR inhibitor, and a c-KIT inhibitor. Examples of the c-MET inhibitor may include PHA-665752, SU11274, XL-880, XL-184, ARQ 197, AMG208, AMG458, CE-355621, and MP470. Example of the EGFR inhibitor may include gefitinib, erlotinib, cetuximab, lapatinib, ZD6474, CL-387785, HKI-272, XL647, PD153035, CI-1033, AEE788, BIBW-2992, EKB-569, and PF-299804. Examples of the ALK inhibitor may include WHI-P154, TAE684, and PF-2341066. Examples of the PDGFR inhibitor may include Gleevec, Desatinib, Valatinib, and Pazopanib. Examples of the c-KIT inhibitor may include Imatinib, Sunitinib, Valatinib, Desatinib, Masitinib, Motesanib, and Pazopanib.

Another preferred example of the subject is a patient with cancer for whom therapeutic effect of the specific anticancer agent is monitored. The patient with cancer may also be a patient who is required to evaluate whether a treatment with the specific anticancer agent should be switched to a treatment with another anticancer agent when a reduction of the therapeutic effect of the specific anticancer agent is observed. The anticancer agent can be the same as those described above.

The biological sample which can be used in the present invention can be a biological sample taken from the aforementioned subject. The biological sample is not particularly limited as long as the fragment of the extracellular domain of c-MET is present therein, and examples of the biological sample may include blood, urine, saliva, ascite, a tissue specimen, a cell specimen, a tissue extract, and a cell extract. Among those mentioned above, the blood, urine and saliva are preferred in terms of low invasiveness. Optionally, the biological sample may be previously treated before the measurement. Examples of such a treatment may include centrifugation, extraction, concentration, fractionation, cell fixation, tissue fixation, tissue freezing, and tissue sectioning.

The measurement of the concentration of the fragment of the extracellular domain of c-MET can be carried out, for example, using a substance having an affinity for the fragment of the extracellular domain of c-MET (which is described later). The measurement may also be carried out by an immunological technique. Examples of such an immunological technique may include an enzyme immunoassay (EIA) (e.g., direct competitive ELISA, indirect competitive ELISA, sandwich ELISA), a radioimmunoassay (RIA), a fluorescence immunoassay (FIA), an immunochromatographic method, a luminescence immunoassay, a spin immunoassay, a western blotting method, and a latex aggregation method. Examples of the method other than the aforementioned methods, which enables the measurement of the fragment of the extracellular domain of c-MET, may include LC-MS.

In the aforementioned (b), the measured concentration of the fragment of the extracellular domain of c-MET can be compared with an indicator which presents a relationship between a concentration of the fragment of the extracellular domain of c-MET and an effect of the anticancer agent on the cancer. The indicator may indicate a relative relationship between a high or low concentration of the fragment of the extracellular domain of c-MET and a strong or weak effect of the anticancer agent (sensitivity or resistance against the anticancer agent). For example, when the measured concentration of the fragment of the extracellular domain of c-MET is relatively high, a therapeutic effect of the c-MET inhibitor is possibly high or a therapeutic effect of the other anticancer agent (e.g., the EGFR inhibitor, ALK inhibitor, PDGFR inhibitor or c-KIT inhibitor as mentioned above) is possibly low. In addition, when the measured concentration of the fragment of the extracellular domain of c-MET is relatively low, a therapeutic effect of the c-MET inhibitor is possibly low or a therapeutic effect of the other anticancer agent (e.g., the EGFR inhibitor, ALK inhibitor, PDGFR inhibitor or c-KIT inhibitor as mentioned above) is possibly high. In the present invention, a specific standard value may be provided as the indicator. As such a standard value, the concentration of the fragment of the extracellular domain of c-MET that can exhibit a high positive rate in a patient sensitive against the c-MET inhibitor or a patient resistant against the other anticancer agent (equal to or more than the standard value) and that can exhibit a high negative rate in a patient resistant against the c-MET inhibitor and a patient sensitive against the other anticancer agent (less than the standard value) may be set up. An example of such a standard value is a cutoff value. A method of calculating the standard value is well-known in the art.

According to the present invention, it can be determined whether a patient with cancer is sensitive or resistant against the specific anticancer agent. Such a determination is useful for deciding on the anticancer agent to be administered to the subject. For example, when the measured concentration of the fragment of the extracellular domain of c-MET is relatively high, the patient with cancer is possibly sensitive against the c-MET inhibitor, and a therapeutic effect of the c-MET inhibitor is possibly high. In addition, in this case, the patient is possibly resistant against the other anticancer agent (e.g., the EGFR inhibitor, ALK inhibitor, PDGFR inhibitor or c-KIT inhibitor as mentioned above), and a therapeutic effect of such an anticancer agent is possibly low. On the other hand, when the measured concentration of the fragment of the extracellular domain of c-MET is relatively low, the patient with cancer is possibly resistant against the c-MET inhibitor, and a therapeutic effect of the c-MET inhibitor is possibly low. In addition, in this case, the patient is possibly sensitive against the other anticancer agent (e.g., the EGFR inhibitor, ALK inhibitor, PDGFR inhibitor, or c-KIT inhibitor as mentioned above), and a therapeutic effect of such an anticancer agent is possibly high.

Furthermore, according to the present invention, a therapeutic effect of the specific anticancer agent can be monitored over time. Such a monitoring is useful for evaluating whether the specific anticancer agent should be switched to another anticancer agent or not when reduction of the therapeutic effect of the anticancer agent is observed. For example, when the measured concentration of the fragment of the extracellular domain of c-MET is kept at relatively high level, the patient with cancer is still possibly sensitive against the c-MET inhibitor and the therapeutic effect of the c-MET inhibitor continues to be possibly high. In addition, in this case, the patient is still possibly resistant against the other anticancer agent (e.g., the EGFR inhibitor, ALK inhibitor, PDGFR inhibitor or c-KIT inhibitor as mentioned above), and the therapeutic effect of such an anticancer agent is possibly low. On the other hand, when the measured concentration of the fragment of the extracellular domain of c-MET is kept at relatively low level, the patient with cancer is still possibly resistant against the c-MET inhibitor and the therapeutic effect of the c-MET inhibitor continues to be possibly low. In addition, in this case, the patient is still possibly sensitive against the other anticancer agent (e.g., the EGFR inhibitor, ALK inhibitor, PDGFR inhibitor or c-KIT inhibitor as mentioned above), and the therapeutic effect of such an anticancer agent continues to be possibly high.

The test method of the present invention may comprise (b') evaluating an effect of the anticancer agent on the cancer on the basis of the measured concentration of the fragment of the extracellular domain of c-MET, in place of the aforementioned (b). This step can be carried out in the same manner as in the aforementioned (b). The test method of the present invention may also comprise deciding the anticancer agent (e.g., the c-MET inhibitor, EGFR inhibitor, ALK inhibitor, PDGFR inhibitor or c-KIT inhibitor as mentioned above) to be administered and/or deciding whether the anticancer agent to be administered should be switched to another anticancer agent (e.g., the c-MET inhibitor, EGFR inhibitor, ALK inhibitor, PDGFR inhibitor or c-KIT inhibitor as mentioned above) or not, based on such a evaluation. The test method of the present invention may further comprise administering the anticancer agent based on such a decision.

The present invention provides a diagnostic reagent for an effect of an anticancer agent on a cancer. The reagent of the present invention comprises a substance having an affinity for the fragment of the extracellular domain of c-MET. The diagnostic reagent of the present invention may be in a form of a kit. The diagnostic reagent of the present invention can be preferably used for carrying out the test method of the present invention.

As used herein, the term "substance having an(the) affinity for a(the) fragment of an(the) extracellular domain of c-MET" refers to a substance having an ability to bind with the fragment of the extracellular domain of c-MET. The substance having an affinity for the fragment of the extracellular domain of c-MET can be a substance having an affinity for the polypeptide consisting of the entire α chain of c-MET or a partial peptide thereof, or a substance having an affinity for the polypeptide consisting of the extracellular region of the β chain of c-MET or a partial peptide thereof. Examples of the substance having an affinity for the fragment of the extracellular domain of c-MET may include antibodies against the fragment of the extracellular domain of c-MET, aptamers against the fragment of the extracellular domain of c-MET, as well as a hepatocyte growth factor (HGF) and HGF mutants retaining an ability to bind to c-MET.

The antibody against the fragment of the extracellular domain of c-MET is not particularly limited as long as the antibody can specifically bind with the fragment of the extracellular domain of c-MET. For example, the antibody against the fragment of the extracellular domain of c-MET may be either a polyclonal antibody or a monoclonal antibody. The antibody may also be fragments (e.g., Fab, F(ab')$_2$) of the antibody, or a recombinant antibody (e.g., scFv). The antibody may be provided in a form of being immobilized on a substrate such as a plate or a form of being immersed in a support such as a strip. The antibody can be produced by a known method per se using the fragment of the extracellular domain of c-MET or the partial peptide thereof (e.g., a partial peptide of the α chain, a partial peptide of the extracellular region of the β chain) as an antigen. The antigen can be produced appropriately with reference to information on an amino acid sequence of c-MET. A fragment of the extracellular domain of c-MET which is obtained from a supernatant of cultured cancer cells may also be used as the antigen.

The polyclonal antibody can be obtained, for example, by administering the fragment of the extracellular domain of c-MET or the partial peptide thereof as the antigen together with a commercially available adjuvant (e.g., complete or incomplete Freund's adjuvant) subcutaneously or intraperitoneally to an animal approximately two to four times every two or three weeks, collecting whole blood about 3 to 10 days after the final immunization, and purifying antiserum. The antigen may be a complex obtained by crosslinking the fragment of the extracellular domain of c-MET or the partial peptide thereof with a carrier protein (e.g., bovine serum albumin or KLH). Examples of the animal administered with the antigen may include mammals such as rats, mice, rabbits, sheeps, cattle, guinea pigs, and hamsters.

The monoclonal antibody can be produced, for example, by a cell fusion method. For example, a mouse is administered with the fragment of the extracellular domain of c-MET or the partial peptide thereof together with the commercially available adjuvant subcutaneously or intraperitoneally two to four times, spleen or lymph node is taken from the mouse about 3 days after the final immunization, and leukocytes are collected. A cell fusion of this leukocyte and a myeloma cell (e.g., NS-1) is carried out to obtain a hybridoma that produces the monoclonal antibody against the fragment or peptide. The cell fusion methods may include a PEG method and a voltage pulse method. The hybridoma that produces a desired monoclonal antibody can be selected by detecting an antibody specifically binding to the antigen in a culture supernatant using a well-known EIA or RIA method or the like. The hybridoma that produced the monoclonal antibody can be cultured in vitro, or in vivo such as in ascites of a mouse or a rat, preferably the mouse, and the antibody can be obtained from the culture supernatant of the hybridoma or from the ascites of the animal.

The aptamer against the fragment of the extracellular domain of c-MET is not particularly limited as long as it can specifically bind to the fragment of the extracellular domain of c-MET. The aptamer can be produced by a technique called SELEX. For example, UUUGACUAUGUCUGACGGGU-CUGUGGUCAAUUCCGCCCC (SEQ ID No:1) disclosed in WO01/009159 is known as the aptamer against the fragment of the extracellular domain of c-MET. Therefore, an aptamer having the nucleotide sequence of SEQ ID NO:1 and mutants thereof retaining an ability to bind with the fragment of the extracellular domain of c-MET may be used as the aptamer. Such mutants may include mutants having a nucleotide sequence having one or several (e.g., 2 to 10, preferably 2 to 5 and more preferably 2 or 3) modified (e.g., substituted, deleted, added, or inserted) nucleotide residues in the nucleotide sequence of SEQ ID NO:1, and retaining an ability to bind with the fragment of the extracellular domain of c-MET.

The hepatocyte growth factor (HGF) is a ligand to c-MET, and the extracellular domain of c-MET has an ability to bind with HGF. Therefore, a natural HGF may be used as the substance having an affinity for the fragment of the extracellular domain of c-MET. An HGF mutant retaining an ability to bind to c-MET may be used as the substance having an affinity for the fragment of the extracellular domain of c-MET. Such mutants may include mutants having an amino acid sequence having one or several (e.g., 2 to 100, preferably 2 to 50 and more preferably 2 to 30, 2 to 20 or 2 to 5) modified (e.g., substituted, deleted, added, or inserted) amino acid residues in an amino acid sequence encoding HGF, and retaining an ability to bind to the fragment of the extracellular domain of c-MET.

The substance having an affinity for the fragment of the extracellular domain of c-MET may be optionally provided in a form of being labeled with a labeling substance. Examples of the labeling substance may include fluorescent substances such as FITC and FAM, luminescent substances such as luminol, luciferin and lucigenin, radioisotopes such as $^3$H, $^{14}$C, $^{32}$P, $^{35}$S, and $^{123}$I, and affinity substances such as biotin and streptoavidin.

The reagent of the present invention may be provided in a form of a kit comprising an additional component in addition to the substance having an affinity for the fragment of the extracellular domain of c-MET. In this case, respective components contained in the kit may be provided in a mutually separated form, e.g., a form of being contained in a different vessel (e.g., tube). For example, when the substance having an affinity for the fragment of the extracellular domain of c-MET is not labeled with the labeling substance, such a kit may further comprise the labeling substance. Such a kit may also comprise the fragment of the extracellular domain of c-MET as a positive control.

When the reagent of the present invention is provided in the form of the kit, the kit may comprise an additional component depending on a type of the substance having an affinity for the fragment of the extracellular domain of c-MET. For example, when the substance having an affinity for the fragment of the extracellular domain of c-MET is the antibody, the kit may further comprise a secondary antibody (e.g., anti-IgG antibody) and a reagent for detecting the secondary antibody.

When the reagent of the present invention is provided in the form of the kit, the kit may further comprise an instrument capable of collecting the biological sample. The instrument capable of collecting the biological sample is not particularly limited as long as the biological sample can be obtained from the subject, and examples of the instrument may include blood collecting instruments such as a syringe.

EXAMPLES

The present invention will be described in more detail with reference to following Examples, but the present invention is not limited thereto.

Example 1

Detection of Fragment of Extracellular Domain of c-MET that is Specific for Cells Sensitive Against c-MET Inhibitor The cell lines H2170 (derived from human squamous cell lung cancer; Nat. Rev. Cancer, 2007; 7: 169-181.) and HCC827 (derived from human non-small cell lung cancer; Clin. Cancer Res., 2006; 12: 7117-7125.) which did not exhibit an amplification of c-MET gene and were not sensitive against a c-MET inhibitor, and the cell line H1993 (derived from human non-small cell lung cancer; Cancer Res., 2007; 67: 2081-2088.) which exhibited the amplification of the c-MET gene and was sensitive against the c-MET inhibitor were cultured at 37° C. and 5% $CO_2$ in RPMI-1640 medium containing 10% fetal calf serum until a cell density reached about 80%, and then cultured for 24 hours in RPMI-1640 medium free from fetal calf serum. After the cultivation, cell extracts and concentrated culture supernatants from each cell line were subjected to SDS-PAGE and then transferred onto a PVDF membrane. Each cell extract was subjected to western blotting using the antibody against the β chain of c-MET (14G9 obtained from Santa Cruz) and the antibody against the α chain of c-MET (EP1454Y obtained from ABCAM). Each concentrated culture supernatant was subjected to the western blotting using the antibody against the α chain of c-MET (EP1454Y). The antibody against the β chain (14G9) recognizes the β chain of the immature c-MET (pro c-MET) and the mature c-MET (non-cleaved form of c-MET). On the other hand, the antibody against the α chain (EP1454Y) is a monoclonal antibody prepared using the partial peptide of the α chain (this chain binds to the extracellular domain of the β chain via a disulfide linkage and is present extracellularly) as the antigen, thus it can recognize the α chain of the immature c-MET (pro c-MET) and the mature c-MET (non-cleaved form of c-MET) and can also recognize the α chain of the fragment of the extracellular domain of c-MET (i.e., secretory form of c-MET).

Figure 1:
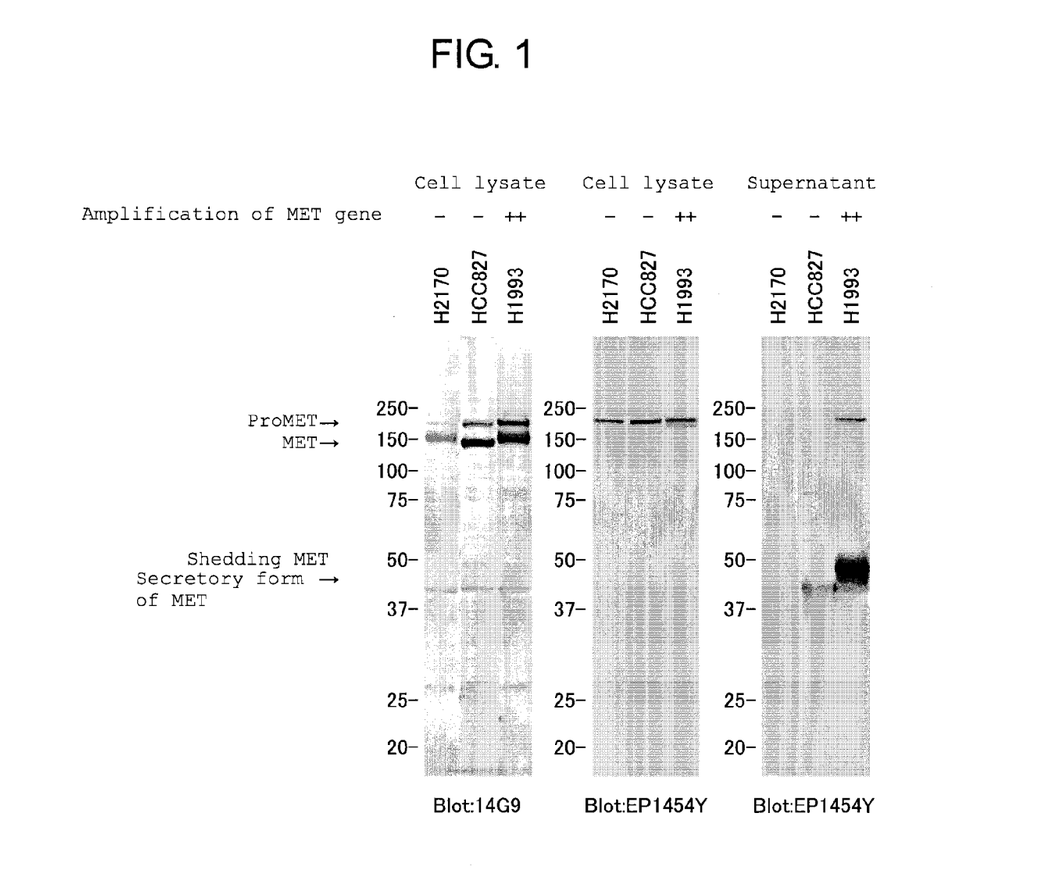
FIG. 1 is a view showing a fragment of an extracellular domain of c-MET detected specifically in a culture supernatant of the cancer cell line H1993 that is sensitive against a c-MET inhibitor. Abbreviations: Pro MET (immature c-MET); MET (mature c-MET); Shedding MET/secretory form MET (fragment of extracellular domain of c-MET)

As a result, no distinct difference was observed for c-MET fragments near 150 kDa detected in the cell lysates between the c-MET inhibitor-insensitive cell lines (H2170 and HCC827) and the c-MET inhibitor-sensitive cell line (H1993) (FIG. 1, Blot: 14G9 and Blot: 1454Y for the cell lysates). This result indicates that the concentrations of the c-METs to be detected in cells, including the immature c-MET (pro c-MET) and the mature c-MET (non-cleaved form of c-MET), can not be correlated with a degree of an amplification of the c-MET gene. On the other hand, the extracellular fragments of c-MET near 40 to 50 kDa were specifically detected in the concentrated culture supernatant of the sensitive cell line (H1993) (FIG. 1, Blot: 1454Y for the supernatant). This result indicates that the concentration of the fragment of the extracellular domain of c-MET (secretory form of c-MET) can be strongly correlated with the degree of the amplification of the c-MET gene.

From the above, it was demonstrated that the cancer sensitive against the c-MET inhibitor, which could be associated with the amplification of the c-MET gene, could be specifically determined by measuring the concentration of the fragment of the extracellular domain of c-MET (secretory form of c-MET).

Example 2

Detection of Fragment of Extracellular Domain of c-MET that is Specific for Gefitinib-Resistant Cells The gefitinib-sensitive cell line HCC827 and a gefitinib-resistant cell line established therefrom were used. Specifically, the gefitinib-resistant cell line (Resistant) was established by passaging HCC827 cells for three months in gefitinib-containing medium according to the method disclosed in Science, 2007; 316: 1039-1043. The gefitinib-sensitive cell line HCC827 and the gefitinib-resistant cell line were cultured at 37° C. and 5% $CO_2$ in RPMI-1640 medium containing 10% fetal calf serum until the cell density reached about 80%, and then cultured in RPMI-1640 medium free from fetal calf serum for 24 hours. After the cultivation, cell extracts and concentrated culture supernatants from each cell line were subjected to SDS-PAGE and then transferred onto a PVDF membrane. Each cell extract was subjected to the western blotting using the antibody against the β chain of c-MET (14G9) and the antibody against the α chain of c-MET (EP1454Y). Each concentrated culture supernatant was subjected to the western blotting using the antibody against the α chain (EP1454Y).

Figure 2:
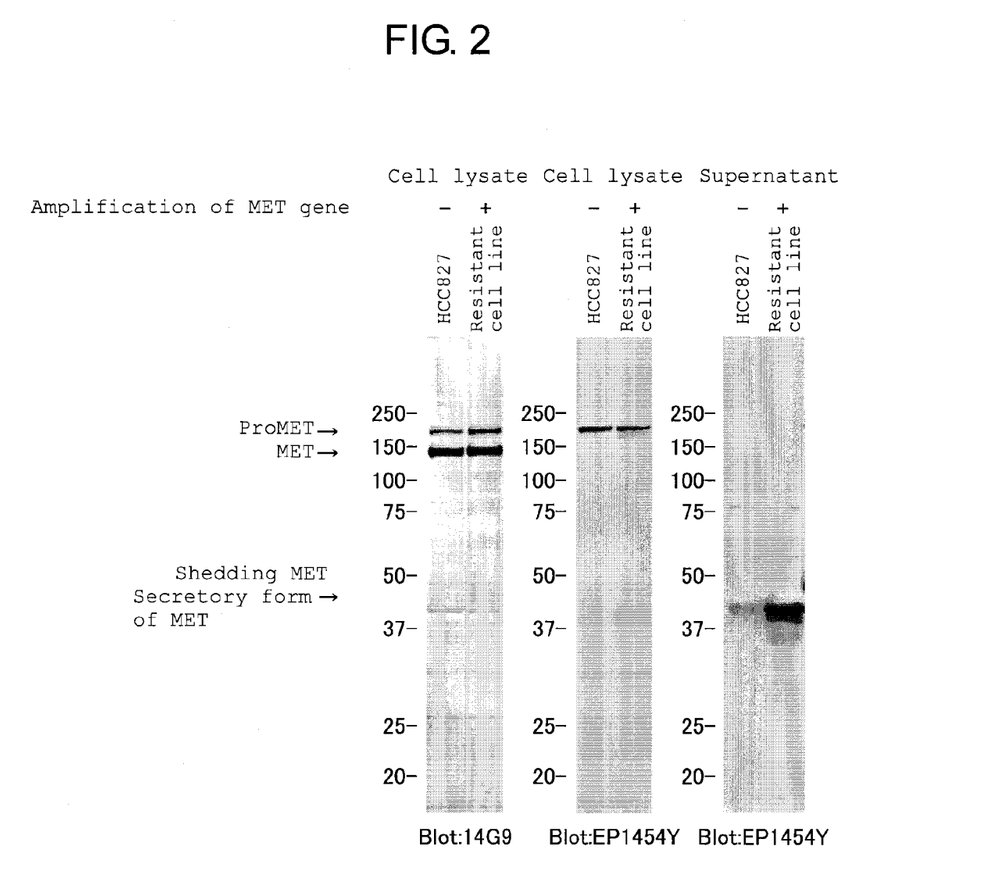
FIG. 2 is a view showing a fragment of an extracellular domain of c-MET detected specifically in a culture supernatant of gefitinib-resistant cell line. The abbreviations are the same as in FIG. 1.

As a result, no distinct difference was observed for c-MET fragments near 150 kDa detected in the cell lysates between the gefitinib-sensitive cell line (HCC827) and the gefitinib-resistant cell line (FIG. 2, Blot: 14G9 and Blot: 1454Y for the cell lysates). This result indicates that the concentrations of the c-METs to be detected in cells, including the immature c-MET (pro c-MET) and the mature c-MET (non-cleaved form of c-MET), can not be correlated with a degree of an amplification of the c-MET gene. On the other hand, the extracellular fragments of c-MET near 40 to 50 kDa were specifically detected in the concentrated culture supernatant of the resistant cell line (FIG. 2, Blot: 1454Y for the supernatant). This result indicates that the concentration of the extracellular fragment of c-MET (secretory form of c-MET) can be strongly correlated with the degree of the amplification of the c-MET gene in the cancer resistant against the anticancer agent (e.g., EGFR inhibitor), the existence of which depends on c-MET.

From the above, it was demonstrated that the cancer resistant against the anticancer agent, which could be associated with the amplification of the c-MET gene, could be specifically determined by measuring the concentration of the fragment of the extracellular domain of c-MET (secretory form of c-MET).

Example 3

Secretion of Fragment of Extracellular Domain of c-MET in Blood that is Specific for c-MET Inhibitor-Sensitive Cells The cell line H2170 which did not exhibit an amplification of c-MET and was not sensitive against a c-MET inhibitor, and the cell line H1993 which exhibited the amplification of the c-MET and was sensitive against the c-MET inhibitor were subcutaneously transplanted in nude mice. After several weeks, blood was collected from the mice that had formed tumor subcutaneously and serum samples were prepared. Amounts of the fragment of the extracellular domain of c-MET present in these serum samples were quantified by ELISA measurement system (Invitrogen).

Figure 3:
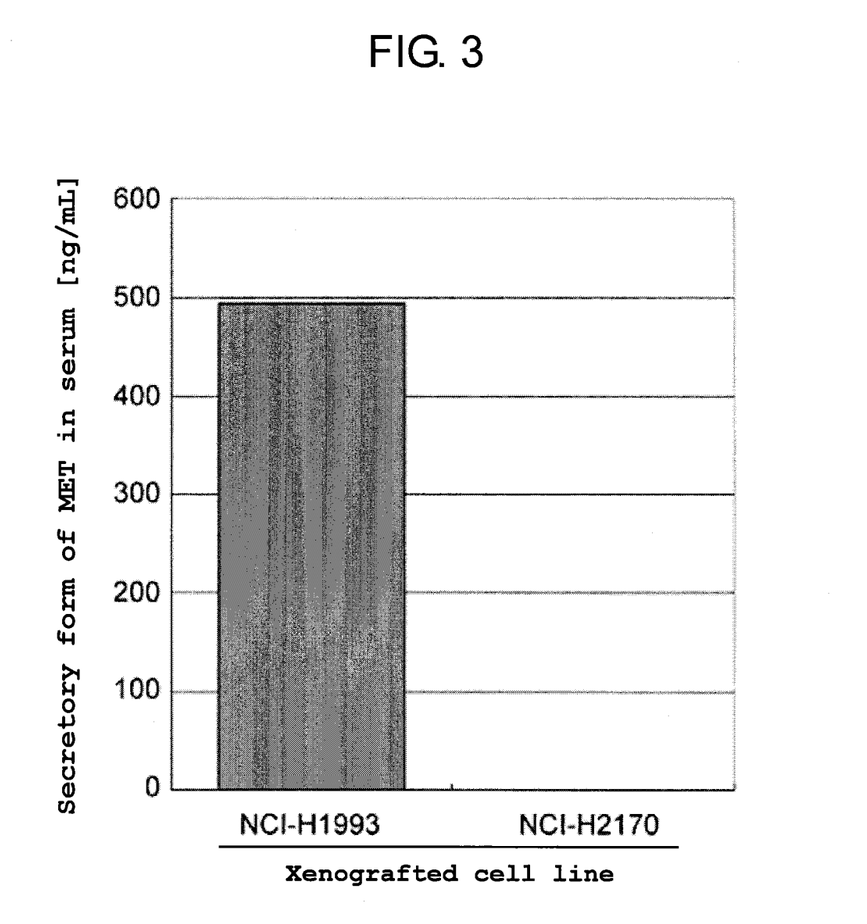
FIG. 3 is a view showing an amount of the fragment of the extracellular domain of c-MET in serum from a mouse transplanted with H1993 (NCI-H1993) and in serum from a mouse transplanted with H2170 (NCI-H2170)
Figure 4:
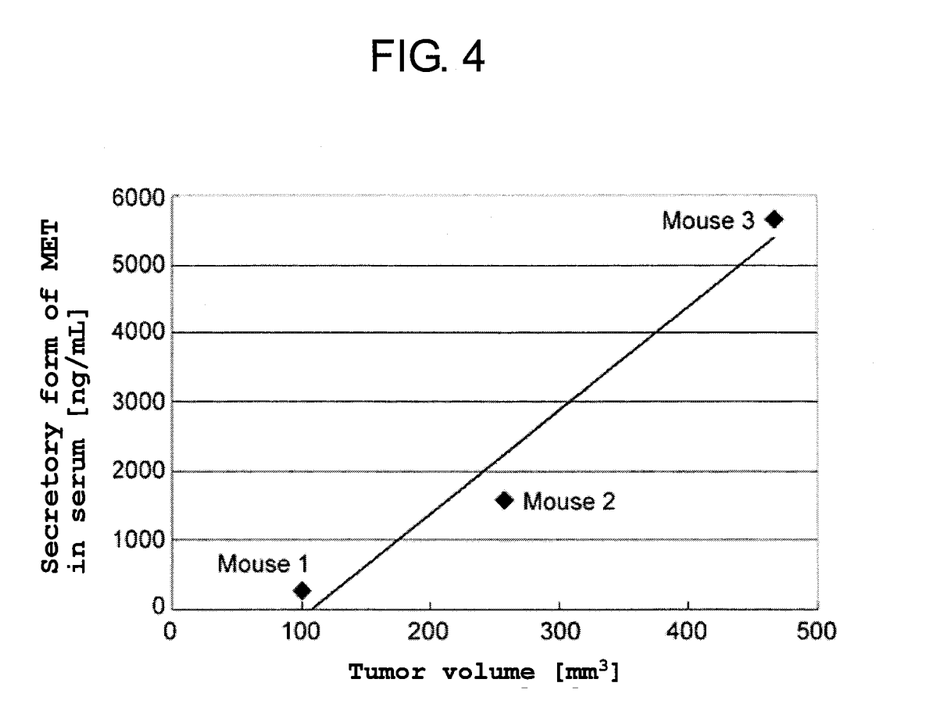
FIG. 4 is a view showing a correlation between amounts of the fragment of the extracellular domain of c-MET in serums and tumor volumes in mice transplanted with H1993.

As a result, the fragment of the extracellular domain of c-MET was clearly detected in the serums from the mice transplanted with H1993 whereas the fragment was not detected at all in the serums from the mice transplanted with H2170 (FIG. 3). The fragment of the extracellular domain of c-MET was quantified in the serums from three mice transplanted with the H1993 that had formed tumor in different size. As a result, the amount of the fragment in the serum exhibited a strong positive correlation with the tumor volume (FIG. 4).

From the above, it was demonstrated that the cancer sensitive against the c-MET inhibitor, which could be associated with the amplification of the c-MET gene, could be specifically determined by measuring the concentration of the fragment of the extracellular domain of c-MET (secretory form of c-MET) in blood from an individual having the cancer.

INDUSTRIAL APPLICABILITY

The present invention is useful for testing an effect of an anticancer agent on a cancer, and is also useful as the diagnostic reagent and the kit.

The invention claimed is:

1. A method for selecting and treating a subject having a lung cancer sensitive to a c-MET inhibitor comprising:
   detecting a secreted fragment of a c-MET extracellular domain in a cell-free portion of a biological sample obtained from the subject having a lung cancer that is EGFR-inhibitor resistant using an antibody or an antigen-binding fragment thereof that binds to c-MET alpha chain of a c-MET extracellular domain,
   selecting a subject having a lung cancer sensitive to treatment with a c-MET inhibitor when said secreted fragment of the c-MET extracellular domain is detected, and
   treating the subject with a c-MET inhibitor selected from the group consisting of PHA-665752, SU11274, XL-880, XL-184, ARQ197, AMG208, AMG458, CD-355621, and MP470.

2. The method of claim 1, wherein said antibody or antigen-binding fragment thereof is monoclonal.

3. The method of claim 1, wherein said detecting comprises contacting said antibody or antigen-binding fragment thereof with the biological sample, which is suspected of containing a C-MET extracellular domain, under conditions suitable for complex formation between the antibody or antigen-binding fragment thereof and a C-MET extracellular domain, and detecting complex formation.

4. The method of claim 1, wherein the subject is a human.

5. The method of claim 1, wherein the lung cancer is a non-small cell carcinoma of the lung.

6. The method of claim 1, wherein the lung cancer is resistant to an EGFR inhibitor other than gefitinib.

7. The method of claim 6, wherein the lung cancer is resistant to gefitinib.

8. The method of claim 1, further comprising taking the biological sample from the subject.

9. A method for selecting and treating a lung cancer patient whose lung cancer is sensitive to a c-MET inhibitor comprising:
   obtaining a biological sample from a lung cancer patient whose lung cancer is EGFR-inhibitor resistant,
   detecting a secreted fragment of a c-MET extracellular domain in a cell-free portion of the sample using an antibody or an antigen-binding fragment thereof that binds to the alpha chain of a c-MET extracellular domain,
   selecting a subject having a lung cancer sensitive to treatment with a c-MET inhibitor when said secreted fragment of the c-MET extracellular domain is detected, and
   treating the subject with a c-MET inhibitor selected from the group consisting of PHA-665752, SU11274, XL-880, XL-184, ARQ197, AMG208, AMG458, CD-355621, and MP470.

* * * * *

SEQUENCE LISTING

<160> NUMBER OF SEQ ID NOS: 1

<210> SEQ ID NO 1
<211> LENGTH: 39
<212> TYPE: RNA
<213> ORGANISM: Homo sapiens

<400> SEQUENCE: 1
uuugacuaug ucugacgggu cuguggucaa uuccgcccc                    39